(12) United States Patent
Oduro

(10) Patent No.: US 10,564,142 B2
(45) Date of Patent: Feb. 18, 2020

(54) QUANTIFYING ORGANIC AND INORGANIC SULFUR COMPONENTS

(71) Applicant: Saudi Arabian Oil Company, Dhahran (SA)

(72) Inventor: Harry Daniel Oduro, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 97 days.

(21) Appl. No.: 15/719,799

(22) Filed: Sep. 29, 2017

(65) Prior Publication Data

US 2019/0101519 A1    Apr. 4, 2019

(51) Int. Cl.
    *G01N 33/26*     (2006.01)
    *G01N 33/28*     (2006.01)

(52) U.S. Cl.
    CPC .................... *G01N 33/287* (2013.01)

(58) Field of Classification Search
    CPC .. G01N 33/287; G01N 33/2835; G01N 33/28; G01N 33/26
    USPC ......................................... 436/123
    See application file for complete search history.

(56) References Cited

U.S. PATENT DOCUMENTS

| | | | |
|---|---|---|---|
| 3,185,641 A | 5/1965 | Cowden | |
| 3,838,969 A | 10/1974 | Dugan | |
| 4,120,659 A | 10/1978 | Cropper | |
| 4,172,705 A | 10/1979 | Castro et al. | |
| 4,213,763 A | 7/1980 | Madec et al. | |
| 4,293,308 A | 10/1981 | Sisti et al. | |
| 4,330,298 A | 5/1982 | Hawn et al. | |
| 4,409,336 A | 10/1983 | Oita | |
| 5,049,508 A | 9/1991 | Hilscher et al. | |
| 5,152,963 A | 10/1992 | Wreyford | |
| 5,250,181 A | 10/1993 | Falkiner et al. | |
| 5,525,233 A | 6/1996 | Falkiner et al. | |
| 6,013,530 A | 1/2000 | Tawara | |
| 6,402,940 B1 | 6/2002 | Rappas | |
| 6,830,830 B2 | 12/2004 | Hsieh et al. | |

(Continued)

OTHER PUBLICATIONS

Backlund et al., "An anlytical procedure for determination of sulphur species and isotopes in boreal acid sulphate soils and sediments," Agriculture and Food Science, vol. 14, No. 1, Jan. 2005, 13 pages.

(Continued)

*Primary Examiner* — Christine T Mui
(74) *Attorney, Agent, or Firm* — Fish & Richardson P.C.

(57) ABSTRACT

Quantifying an amount of sulfur in a petroleum sample includes sequential extraction and quantification of inorganic and organic sulfur species. An exemplary process includes extracting inorganic sulfur components from the sample to yield extracted inorganic sulfur components and a residual sample, and reducing the sulfur in the extracted inorganic sulfur components to yield a first quantity of hydrogen sulfide. The organic sulfur components are extracted from the residual sample to yield extracted organic sulfur components, and the sulfur in the extracted organic sulfur components is reduced to yield a second quantity of hydrogen sulfide. The amount of sulfur in the first quantity of hydrogen sulfide and the amount of sulfur in the second quantity of hydrogen sulfide are combined to yield a total amount of sulfur in the sample.

22 Claims, 8 Drawing Sheets

(56) References Cited

U.S. PATENT DOCUMENTS

| | | | |
|---|---|---|---|
| 7,025,138 B2* | 4/2006 | Kurkjian | E21B 49/081 |
| | | | 166/113 |
| 7,141,211 B2 | 11/2006 | Aktiengesellschaft | |
| 7,214,345 B1 | 5/2007 | Sullivan et al. | |
| 7,632,396 B2 | 12/2009 | Feimer | |
| 7,744,749 B2 | 6/2010 | Martinie et al. | |
| 8,016,999 B2 | 9/2011 | Borgna et al. | |
| 2003/0134426 A1* | 7/2003 | Jiang | E21B 47/011 |
| | | | 436/121 |
| 2006/0011516 A1 | 1/2006 | Feimer et al. | |
| 2015/0087075 A1* | 3/2015 | Chughtai | G01N 33/383 |
| | | | 436/123 |
| 2015/0224873 A1* | 8/2015 | Ishitoya | F02M 37/025 |
| | | | 123/509 |

OTHER PUBLICATIONS

Damste, "Chapter 26—Characterization of Organically Bound Sulfur in High-Molecular-Weight, Sedimentary Organic Matter using Flash Pyrolysis and Raney Ni Desulfurization," in Geochemistry of Sulfur in Fossil Fuels, American Chemical Society, Dec. 31, 1990, 43 pages.

Rosenberg et al., "Study of thermal maturation processes of sulfur-rich source rock using compound specific sulfur isotope analysis," Organic Geochemistry, vol. 112, Jun. 22, 2017, 16 pages.

Watkinson, "Measurement of elemental sulfur in soil and sediments—Field sampling, sample storage, pretreatment, extraction and analysis by high performance liquid chromatography," Australian Journal of Soil Research, Dec. 31, 1987, 5 pages.

International Search Report and Written Opinion issued in International Application No. PCT/US2018/053045 dated Feb. 12, 2019, 15 pages.

Alexio et al. "Determination of Total Sulphur in Ethanol by Reduction Using Raney Nickel and Detection by Cathodic Stripping Voltammetry," Analyst, Sep. 1988, vol. 113, 3 pages.

Canfield et al. "The Use of Chromium Reduction in the Analysis of Reduced Inorganic Sulfur in Sediments and Shales," Chemical Geology, 54./1-2, Jan. 30, 1986, 8 pages.

Cline. "Spectrophotometric Determination of Hydrogen Sulfide in Natural Waters," Limonolgy and Oceanography 14.3, May 1, 1969, 5 pages.

Groger et al. "Quantitative Recovery of Elemental Sulfur and Improved Selectivity in a Chromium-Reducible Sulfur Distillation," Geostandards and Geoanalytical Research, vol. 33.1, Mar. 1, 2009, 11 pages.

Shah et al. "Raney Nickel Reductions—Part 1," Proceedings of the Indian Academy of Science, Sep. 1948, 28:142, 9 pages.

Thode et al. "Sulphur isotope geochemistry," Geochimica et cosmochimica Acta, vol. 25, Nov. 1961, 17 pages.

* cited by examiner

TABLE 1. CHEMICAL REAGENTS AND REACTION CONDITIONS FOR SEQUENTIAL SULFUR EXTRACTION

| CHEMICAL EXTRACTANTS | SULFUR PHASE DISSOLVED | REACTION TIME (HOURS) | VOLUME OF Zn(OAc) CAPTURING SOLUTION |
|---|---|---|---|
| 5.0M HCl solution - 1g sample/10 mL | Acid Volatile sulfide - AVS (FeS, HS-, $H_2S$, $Fe_{(1-x)}S$) | 2 | 40 mL - 0.2g of S/10 mL of 5% Zn(OAc) |
| 1.0M $CrCl_2$/1.0M HCl - 1g sample/10 mL | Pyrite - ($FeS_2$) | 2 | 40 mL - 0.1g of S/10 mL of 5% Zn(OAc) |
| 15.0mL EtOH/15.0mL acidified $CrCl_2$ - 1g sample/10 mL | Elemental Sulfur - ($S_8$) | 2 | 40 mL - 0.1g of S/10 mL of 5% Zn(OAc) |
| 15.0mL HCl/10.0mL HI/5.0mL $H_3PO_4$ - 1g sample/10 mL | Sulfate - ($SO_4^{2-}$) | 2.5 | 40 mL - 0.1g of S/10 mL of 5% Zn(OAc) |
| 50.0mL DCM/50.0 mL MeOH + 1g Ni-$H_2$ catalyst/20mL HCl | Bitumen Sulfur | 1.5 | 40 mL - 0.1g of S/10 mL of 5% Zn(OAc) |
| 25.0mL EtOH/1g Ni-$H_2$ catalyst/1.0g Al(OH)$_3$ | Kerogen Sulfur | 1.5 | 40 mL - 0.1g of S/10 mL of 5% Zn(OAc) |

Where Et=Ethanol; DCM=Dichloromethane; Ni-$H_2$=Raney nickel catalyst; Me=Methanol; Zn(OAc)= Zinc acetate.
Note - All sulfur phases were reduced as $H_2S$ and captured ZnS for VU-VIS analyses

FIG. 9

TABLE 2. SULFUR CONTENT OF PETROLEUM SOURCE ROCK SAMPLES

| LOCATION 1 - DRILL CORE SAMPLES | AVS/ [Wt%] | CRS/ [Wt%] | $S_8$/ [Wt%] | $SO_4^{2-}$/ [Wt%] | BITUMEN SULFUR/ [Wt%] | KEROGEN SULFUR/ [Wt%] | TOTAL SULFUR (Est. Seq. Extraction)/[Wt%] |
|---|---|---|---|---|---|---|---|
| L-11 | 0.27 | 0.23 | 0.16 | 0.13 | 0.20 | 0.24 | 1.227 |
| L-12 | 1.06 | 1.12 | 0.21 | 0.18 | 0.24 | 0.46 | 3.272 |
| L-13 | 0.46 | 1.04 | 0.17 | 0.20 | 0.19 | 0.38 | 2.435 |
| L-14 | 0.13 | 0.12 | 0.05 | 0.10 | 0.11 | 0.21 | 0.716 |
| L-15 | 0.09 | 0.13 | 0.16 | 0.02 | 0.05 | 0.07 | 0.516 |
| L-16 | 0.34 | 0.57 | 0.16 | 0.17 | 0.11 | 0.21 | 1.554 |
| L-17 | 1.20 | 1.09 | 0.48 | 0.13 | 0.36 | 0.59 | 3.854 |
| L-18 | 0.78 | 0.37 | 0.99 | 0.11 | 0.25 | 0.35 | 2.850 |
| L-19 | 2.23 | 2.61 | 0.64 | 0.13 | 0.42 | 0.70 | 6.729 |
| L-110 | 1.23 | 2.09 | 0.47 | 0.40 | 0.65 | 0.99 | 5.832 |
| LOCATION 2 - DRILL CORE SAMPLES | AVS/ [Wt%] | CRS/ [Wt%] | $S_8$/ [Wt%] | $SO_4^{2-}$/ [Wt%] | BITUMEN SULFUR/ [Wt%] | KEROGEN SULFUR/ [Wt%] | TOTAL SULFUR (Est. Seq. Extraction)/[Wt%] |
| L21 | 0.07 | 0.09 | 0.06 | 0.01 | 0.01 | 0.04 | 0.282 |
| L22 | 0.10 | 0.08 | 0.04 | 0.12 | 0.05 | 0.07 | 0.459 |
| L23 | 0.09 | 0.06 | 0.03 | 0.02 | 0.02 | 0.07 | 0.297 |
| L24 | 0.07 | 0.08 | 0.02 | 0.01 | 0.03 | 0.05 | 0.264 |
| L25 | 0.11 | 0.09 | 0.03 | 0.01 | 0.04 | 0.03 | 0.316 |
| LOCATION 3 - DRILL CORE SAMPLES | AVS/ [Wt%] | CRS/ [Wt%] | $S_8$/ [Wt%] | $SO_4^{2-}$/ [Wt%] | BITUMEN SULFUR/ [Wt%] | KEROGEN SULFUR/ [Wt%] | TOTAL SULFUR (Est. Seq. Extraction)/[Wt%] |
| L31 | 0.26 | 0.48 | 0.07 | 0.05 | 0.13 | 0.28 | 1.269 |
| L32 | 0.24 | 0.07 | 0.04 | 0.02 | 0.10 | 0.17 | 0.639 |
| L33 | 0.03 | 0.06 | 0.04 | 0.02 | 0.09 | 0.10 | 0.335 |
| L34 | 0.09 | 0.10 | 0.02 | 0.02 | 0.06 | 0.06 | 0.357 |
| L35 | 0.10 | 0.12 | 0.03 | 0.05 | 0.10 | 0.31 | 0.710 |

FIG. 10

TABLE 3. COMPARISON OF TOTAL SULFUR CONTENT

| LOCATION 1 - DRILL CORE SAMPLES | TOTAL SULFUR (Est. Seq. Extraction)/[Wt%] | TOTAL SULFUR (Elemental Analyzer)/[Wt%] | ESTIMATED ANALYTICAL ERROR |
|---|---|---|---|
| L-11 | 1.227 | 1.253 | -0.026 |
| L-12 | 3.272 | 3.122 | 0.150 |
| L-13 | 2.435 | 2.419 | 0.016 |
| L-14 | 0.716 | 0.690 | 0.026 |
| L-15 | 0.516 | 0.525 | -0.009 |
| L-16 | 1.554 | 1.549 | 0.005 |
| L-17 | 3.854 | 3.845 | 0.009 |
| L-18 | 2.850 | 2.937 | -0.087 |
| L-19 | 6.729 | 6.719 | 0.010 |
| L-110 | 5.832 | 5.828 | 0.004 |
|  |  | MEAN ANALYTICAL ERROR | 0.098 |
| LOCATION 2 - DRILL CORE SAMPLES | TOTAL SULFUR (Est. Seq. Extraction)/[Wt%] | TOTAL SULFUR (Elemental Analyzer)/[Wt%] | ESTIMATED ANALYTICAL ERROR |
| L21 | 0.282 | 0.226 | 0.056 |
| L22 | 0.459 | 0.391 | 0.067 |
| L23 | 0.297 | 0.277 | 0.020 |
| L24 | 0.264 | 0.227 | 0.038 |
| L25 | 0.316 | 0.306 | 0.009 |
|  |  | MEAN ANALYTICAL ERROR | 0.191 |
| LOCATION 3 - DRILL CORE SAMPLES | TOTAL SULFUR (Est. Seq. Extraction)/[Wt%] | TOTAL SULFUR (Elemental Analyzer)/[Wt%] | ESTIMATED ANALYTICAL ERROR |
| L31 | 1.269 | 1.242 | 0.027 |
| L32 | 0.639 | 0.637 | 0.002 |
| L33 | 0.335 | 0.329 | 0.006 |
| L34 | 0.357 | 0.346 | 0.010 |
| L35 | 0.710 | 0.652 | 0.058 |
|  |  | MEAN ANALYTICAL ERROR | 0.103 |

FIG. 11

QUANTIFYING ORGANIC AND INORGANIC SULFUR COMPONENTS

TECHNICAL FIELD

This disclosure relates to quantifying organic and inorganic sulfur in petroleum material.

BACKGROUND

Sulfur is the third most abundant element in petroleum, occurring in certain heavy oils at concentrations of over 12 weight percent (wt %). Reserves of low sulfur crude oils are depleting worldwide, necessitating the identification of reservoirs of crude oils with high sulfur content. The abundance of sulfur species in hydrocarbon products causes corrosion to infrastructure, health exposure risks, and higher operational and production costs. As a result, environmental regulatory agencies in the world continue to promulgate more stringent regulations towards sulfur emission from fuels and sulfur gases emanating from oil and gas industries.

Methods employed in the petroleum industry to quantify sulfur typically include bulk sample analysis via oxidation, combustion, and other chemical reactions that yield erroneous results caused by masking and matrix effects of other compounds in the samples. In addition, reproducibility and precision of these methods are impractical for quantifying specific sulfur species expected to affect both upstream and downstream operations. Thus, these methods have limited use in hydrocarbon industries for proper characterization and quantification of sulfur content in petroleum products.

SUMMARY

This disclosure describes sequential extraction and quantification of inorganic and organic sulfur species in petroleum materials.

In a general aspect, quantifying an amount of sulfur in a sample having inorganic sulfur components and organic sulfur components includes extracting inorganic sulfur components from the sample to yield extracted organic sulfur components and a residual sample, and reducing the sulfur in the extracted inorganic sulfur components to yield a first quantity of hydrogen sulfide. Organic sulfur components are extracted from the residual sample to yield extracted organic sulfur components, and the sulfur in the extracted organic sulfur components is reduced to yield a second quantity of hydrogen sulfide. The amount of the sulfur in the first quantity of hydrogen sulfide and the second quantity of hydrogen sulfide is quantified.

Implementations of the general aspect may include one or more of the following features.

The sample may include a solid, a liquid, or a mixture thereof.

In some implementations, extracting the inorganic sulfur components from the sample includes sequentially extracting acid volatile sulfur components, pyritic sulfur components, elemental sulfur components, and sulfated sulfur components from the sample.

In some implementations, extracting the inorganic sulfur components from the sample to yield the extracted inorganic sulfur components and the residual sample includes extracting acid volatile sulfur components from the sample to yield extracted acid volatile sulfur components and a first intermediate residual sample, and reducing the sulfur in the extracted inorganic sulfur components to yield the first quantity of hydrogen sulfide includes reducing the sulfur in the extracted volatile sulfur components to yield a first intermediate quantity of hydrogen sulfide. The acid volatile sulfur components typically include at least one of hydrogen sulfide, ($H_2S$), bisulfide ($HS^-$), disulfide ($S^{2-}$), and iron sulfide (FeS). In some cases, extracting the acid volatile sulfur components from the sample includes contacting the sample with hydrochloric acid.

In some implementations, extracting the inorganic sulfur components from the sample to yield the extracted inorganic sulfur components and the residual sample includes extracting pyritic sulfur components from the first intermediate residual sample to yield extracted pyritic sulfur components and a second intermediate residual sample, and reducing the sulfur in the inorganic sulfur components to yield the first quantity of hydrogen sulfide and the residual sample includes reducing the sulfur in the extracted pyritic sulfur components to yield a second intermediate quantity of hydrogen sulfide. The pyritic sulfur components typically include iron disulfide ($FeS_2$). In some cases, extracting the pyritic sulfur components from the first intermediate residual example includes contacting the first intermediate residual sample with chromium reduction acid distillation mixed solvents.

In some implementations, extracting the inorganic sulfur components from the sample to yield the inorganic sulfur components and the residual sample includes extracting elemental sulfur components from the second intermediate residual sample to yield extrated elemental sulfur components and a third intermediate residual sample, and reducing the sulfur in the inorganic sulfur components to yield the first quantity of hydrogen sulfide includes reducing the sulfur in the extracted elemental sulfur components to yield a third intermediate quantity of hydrogen sulfide. The elemental sulfur components typically include at least one of octasulfur ($S_8$) and zero-valent sulfur. In some cases, extracting the elemental sulfur components from the second intermediate residual sample includes contacting the second intermediate residual sample with a mixture of chloroform and methanol.

In some implementations, extracting the inorganic sulfur components from the sample to yield extracted inorganic sulfur components and the residual sample includes extracting sulfated sulfur components from the third intermediate residual sample to yield extracted sulfated sulfur components and a fourth intermediate residual sample, and reducing the sulfur in the extracted inorganic sulfur components to yield the first quantity of hydrogen sulfide includes reducing the sulfur in the extracted sulfated sulfur components to yield a fourth intermediate quantity of hydrogen sulfide. The sulfated sulfur components typically include $SO_4^{2-}$. In some cases, extracting the sulfated sulfur components includes forming a sulfate precipitate, and reducing the sulfur in the extracted sulfated sulfur components to yield a fourth intermediate quantity of hydrogen sulfide includes reducing the sulfate in the sulfate precipitate to yield elemental sulfur, and reducing the elemental sulfur.

In some implementations, extracting the organic sulfur components from the residual sample includes sequentially extracting bitumen sulfur components and kerogen sulfur components from the residual sample.

In some implementations, extracting the organic sulfur components from the residual sample to yield extracted organic sulfur components includes extracting bitumen sulfur components from the residual sample, and reducing the sulfur in the extracted organic sulfur components to yield the second quantity of hydrogen sulfide includes reducing the sulfur in the extracted bitumen sulfur components to yield a fifth intermediate quantity of hydrogen sulfide and a fifth intermediate residual sample. In some cases, extracting the bitumen sulfur components from the fifth intermediate residual sample includes extracting the bitumen sulfur components from the fifth intermediate residual sample with an azeotropic mixture of dichloromethane and methanol, and reducing the sulfur in the extracted bitumen sulfur components via a Raney nickel desulfurization process.

In some implementations, extracting the organic sulfur components from the residual sample to yield the extracted organic sulfur components includes extracting kerogen sulfur components from the fifth intermediate residual sample to yield the extracted kerogen sulfur components, and reducing the sulfur in the extracted organic sulfur components to yield the second quantity of hydrogen sulfide includes reducing the sulfur in the extracted kerogen sulfur components to yield a sixth intermediate quantity of hydrogen sulfide. Reducing the sulfur in the extracted kerogen sulfur components typically includes using a modified Raney nickel and bayerite as a reducing agent.

In some implementations, quantifying the amount of sulfur in the first quantity of hydrogen sulfide includes contacting the first quantity of hydrogen sulfide with a zinc acetate buffer solution to yield zinc sulfide, and quantifying the amount of sulfide in the zinc sulfide. Quantifying the amount of sulfide in the zinc sulfide typically includes a colorimetric determination.

Methods described in this disclosure provide an accurate, robust, and comprehensive approach for sulfur analysis in petroleum materials. These methods are suitable for commercial implementation and allow efficient assessment of the composition and amount of sulfur species in a wide variety of sulfur-bearing petroleum materials, including sulfur components that are likely to be resistant to hydrodesulfurization processes during production and refinery processes. This quantification provides detailed information regarding availability, partitioning, and extent of sulfur distribution in petroleum products, and can be used to pinpoint targets in exploration, production, and refinery processes.

The details of one or more implementations of the subject matter described in this specification are set forth in the accompanying drawings and the following description. Other features, aspects, and advantages of the subject matter will become apparent from the description, the drawings, and the claims.

BRIEF DESCRIPTION OF THE DRAWINGS

FIG. 9 is a table listing reaction conditions and reagents for an example sequential extraction process using the apparatus depicted in FIG. 8.

FIG. 10 is a table summarizing sulfur content of core samples subjected to a sequential extraction process using the apparatus depicted in FIG. 8 and the reaction conditions and reagents listed in the table in FIG. 9.

FIG. 11 is a table comparing sulfur content of core samples assessed via a sequential extraction process and elemental analysis by combustion methods.

DETAILED DESCRIPTION

Sequential extraction and quantification of inorganic sulfur components and organic sulfur components from petroleum materials is described. Inorganic sulfur components include acid volatile sulfur (AVS), pyritic sulfur, elemental sulfur, and sulfated sulfur. Examples of AVS components include hydrogen sulfide ($H_2S$), bisulfide ($HS^-$), disulfide ($S^{2-}$), and iron sulfide (FeS). Pyritic sulfur includes iron disulfide ($FeS_2$). Examples of elemental sulfur include octasulfur ($S_8$) and zero-valent sulfur. Sulfated sulfur components include $SO_4^{2-}$. Organic sulfur components include bitumen-bound sulfur components (referred to as "bitumen sulfur components") and kerogen-bound sulfur components (referred to as "kerogen sulfur components").

Figure 1:
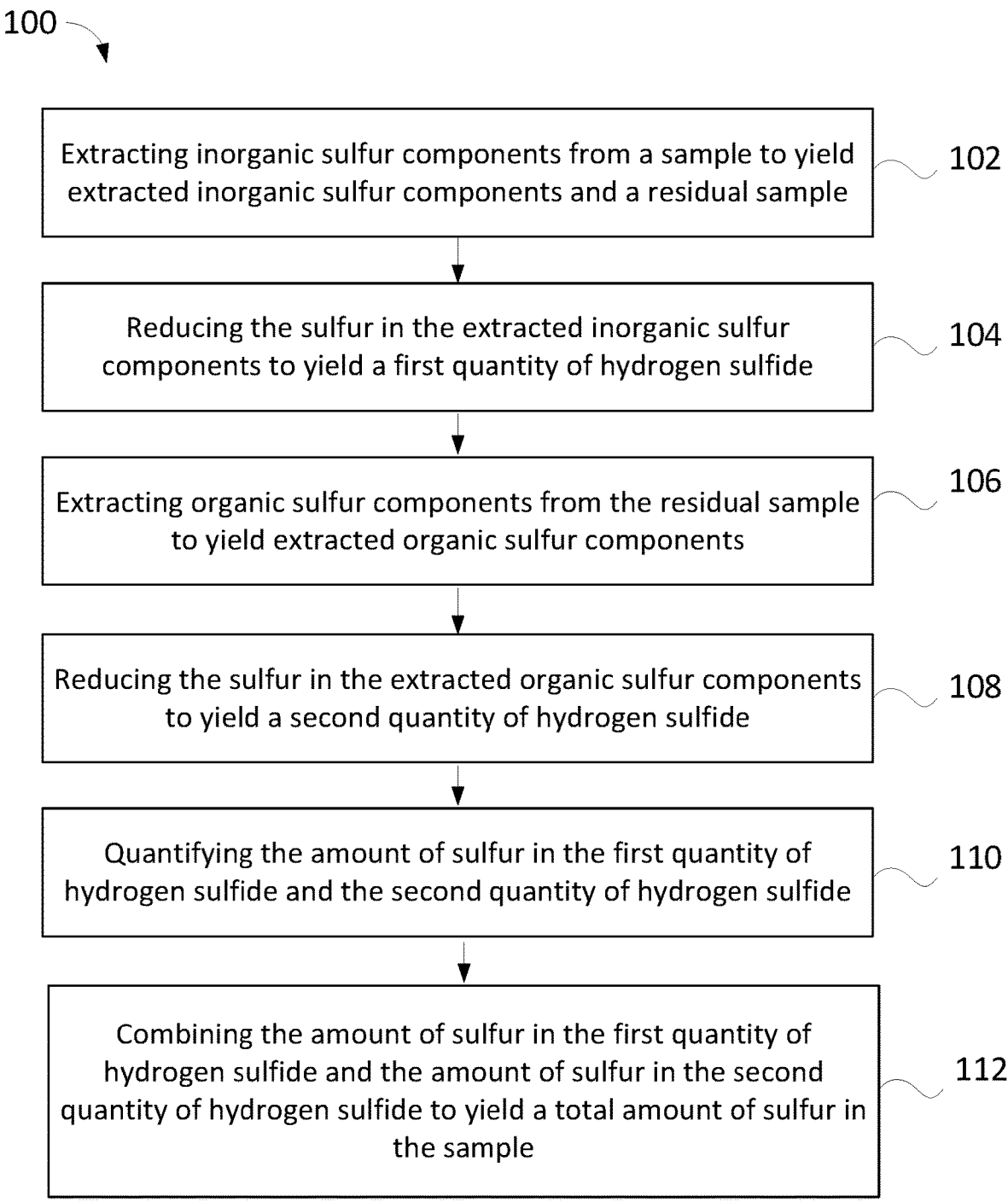
FIG. 1 is a flowchart showing operations in a process for quantifying an amount of sulfur in a sample including inorganic sulfur components and organic sulfur components.

FIG. 1 is a flowchart showing operations in process 100 for quantifying an amount of sulfur in a sample including inorganic sulfur components and organic sulfur components. Suitable samples include solid and liquid sulfur-bearing petroleum materials, such as petroleum source rocks and hydrocarbon condensates. Sulfur-bearing petroleum source rocks, for example, from core samples, may be cut, crushed, and ground to yield a particulate sample before sulfur components are extracted from the sample. In one example, a petroleum source rock sample size is 5 to 10 grams (g). In another example, a hydrocarbon condensate sample size is 5 to 10 milliliters (mL). Process 100 is suitable for detecting sulfur in a sample having a sulfur content of at least 0.1 to 0.2 parts per million (ppm) by weight (for example, 0.15 ppm by weight). Quantification of sulfur via process 100 can be achieved with a relative standard deviation of less than 10%.

In 102, different inorganic sulfur components are extracted from the sample to yield extracted inorganic sulfur components and a residual. The residual sample typically contains solid and dissolved carbon-bonded bitumen and carbon-bonded kerogen sulfur components. Extracting the inorganic sulfur components from the sample may include sequentially extracting AVS components, pyritic sulfur components, elemental sulfur components, and sulfated sulfur components from the sample. In 104, the sulfur in the extracted inorganic components is reduced to yield a first quantity of hydrogen sulfide. Reduction of the sulfur in the inorganic sulfur components can be achieved by combining the extracted inorganic sulfur components with suitable reagents, such as a solvent and a reducing agent as appropriate. The resulting mixture may be heated, for example, under reflux, to release hydrogen sulfide. The released hydrogen sulfide can be condensed to facilitate handling, storage, or both. Extracting and reducing the inorganic sulfur components is described in more detail with respect to FIGS. 2-5.

In 106, organic sulfur components are extracted from the residual sample after all or substantially all of the inorganic sulfur components have been removed to yield extracted organic sulfur components. Extracting the organic sulfur components from the residual sample may include sequentially extracting bitumen sulfur components and kerogen sulfur components from the residual sample. In 108, the sulfur in the extracted organic sulfur components is reduced to yield a second quantity of hydrogen sulfide. Extracting and reducing the organic sulfur components is described in more detail with respect to FIGS. 6-7.

In 110, the amount of sulfur in the first quantity of hydrogen sulfide and the second quantity of hydrogen sulfide is quantified. Quantifying the hydrogen sulfide may be achieved by forming an insoluble sulfide from the hydrogen sulfide. Forming an insoluble sulfide may include contacting the hydrogen sulfide with a suitable capturing solution, such as a zinc acetate buffer solution or a silver nitrate solution, to yield zinc sulfide or silver sulfide, respectively. A suitable zinc acetate buffer solution may be prepared by dissolving 1 g of zinc acetate in 25 mL water, followed by dropwise addition of 0.1 Molar (M) nitric acid. A suitable silver nitrate solution may be prepared by forming an aqueous solution including 5 wt % silver nitrate. Hydrogen sulfide provided to the capturing solution reacts quantitatively to yield a sulfide precipitate.

Methods of quantification of sulfide in insoluble sulfides such as zinc sulfide and silver sulfide are generally known. In one example, an amount of sulfur in zinc sulfide is quantified colorimetrically via ultraviolet-visible (UV-VIS) spectrophotometric analysis. To quantify the sulfur in an amount of zinc sulfide, a zinc sulfide sample is combined with a volume of Cline's reagent. Cline's reagent may be prepared by forming a mixture including 2 g N,N-dimethyl-p-phenylenediamine and 3 g ferric chloride ($FeCl_3$) in 50 mL 50% hydrochloric acid (HCl) cooled to 4 degrees Celsium (° C.). In one example, 1 mL of Cline's reagent is combined with a 9 mL aqueous sample including zinc sulfide. The zinc sulfide reacts with the N,N-dimethyl-p-phenylenediamine in the presence of zinc acetate and ferric chloride under acidic conditions to yield methylene blue according to the following reaction.

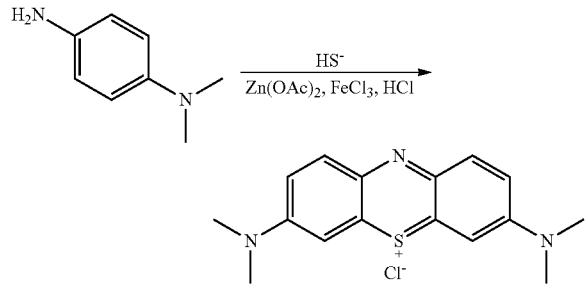

Methylene blue absorbs visible light at a wavelength of 670 nanometers (nm), and can be measured quantitatively using a UV-VIS spectrophotometer. An amount of sulfur in a sample can be quantified by comparing the absorbance at 670 nm of a sample solution with the absorbance at 670 nm of reduced sulfanilamide standards and a blank solution. For a sample containing more than 1.3 g sulfur, average recovery was demonstrated to be 97.1±0.7% (2δ).

In 112, the amount of sulfur in the first quantity of hydrogen sulfide and the amount of sulfur in the second quantity of hydrogen sulfide are combined to yield a total amount of sulfur in the sample. In some cases, the total amount of sulfur in the sample is obtained by quantifying the amount of sulfur in each inorganic sulfur component and each organic sulfur component, and summing the individual amounts from each component to yield a total amount of sulfur in the sample. That is, the total amount of sulfur in the sample may be obtained as a sum of the amount of sulfur from inorganic sulfur components in the sample and the amount of sulfur from organic sulfur components in the sample, where the amount of sulfur from inorganic sulfur components in the sample is a sum of the amount of sulfur in each of the AVS components, pyritic sulfur components, elemental sulfur components, and sulfated sulfur components, and the amount of sulfur from the organic sulfur components is a sum of the amount of sulfur in each of the bitumen sulfur components and kerogen sulfur components.

In some implementations, process 100 may include additional operations not depicted in FIG. 1. In some implementations, one or more operations in process 100 may be omitted. In certain implementations, an order of operations in process 100 may be altered. In one example, AVS components are extracted from a sample, reduced to yield hydrogen sulfide, and the hydrogen sulfide is quantified before other inorganic sulfur components are extracted from the sample, before organic sulfur components are extracted from the residual, or both. Similarly, pyritic sulfur components, elemental sulfur components, and sulfated sulfur components may be sequentially extracted and sequentially quantified, and bitumen sulfur components may be quantified before kerogen sulfur components are extracted.

Extracting the inorganic sulfur components from the sample may include sequentially extracting AVS components, pyritic sulfur components, elemental sulfur components, and sulfated sulfur components, as described with respect to FIGS. 2-5.

Figure 2:
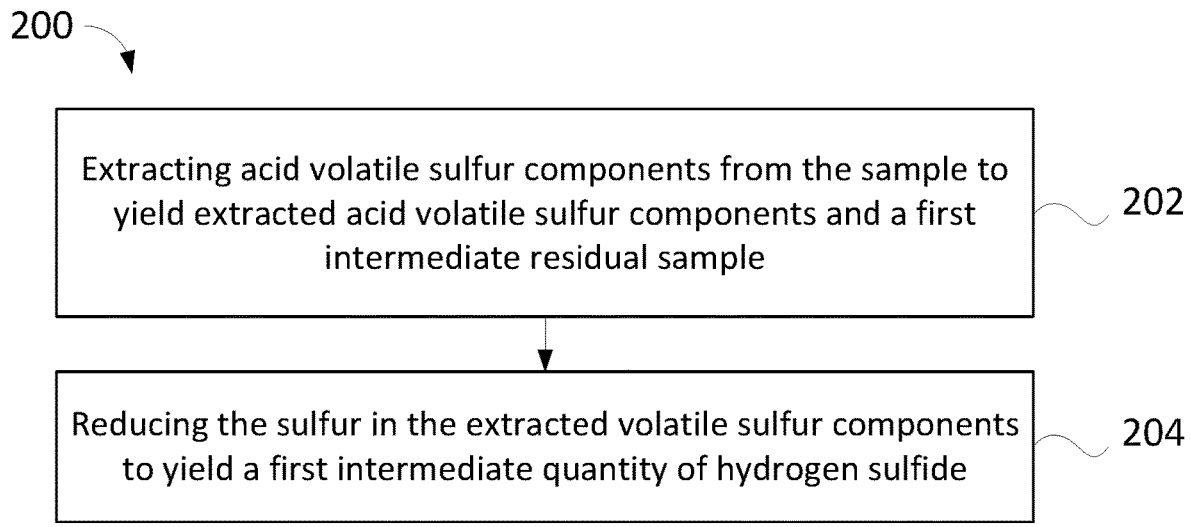
FIG. 2 is a flowchart showing operations in a process for treating the sample described with respect to FIG. 1.

FIG. 2 is a flowchart showing operations in process 200 for treating the sample described with respect to FIG. 1. In 202, AVS components, such as hydrogen sulfide ($H_2S$), bisulfide ($HS^-$), disulfide ($S^{2-}$), and iron sulfide (FeS), are extracted from the sample to yield extracted AVS components and a first intermediate dissolved and solid residual sample. Extracting AVS components from the sample typically includes contacting the sample with an amount of hydrochloric acid at a temperature and for a duration sufficient to extract at least about 99 wt % of the AVS components from the sample. Contacting can include mixing the sample with the hydrochloric acid to yield a mixture and agitating the mixture. A suitable concentration of the hydrochloric acid is 5M, however other concentrations may also be used. A suitable temperature of the hydrochloric acid is in a range between 90° C. and 110° C. In one example, a temperature of the hydrochloric acid is in a range between 92° C. and 109° C. A suitable duration of contacting the sample with the hydrochloric acid is 1 to 3 hours (h). In one example, a duration of contacting the sample with the hydrochloric acid is about 2 h. For 5M hydrochloric acid at a temperature in a range between 92° C. and 109° C., 10 to 15 mL of hydrochloric acid is sufficient to extract AVS components from a 1 g sample of sulfur-bearing petroleum source rock.

In 204, the sulfur in the AVS components is reduced to yield a first intermediate quantity of hydrogen sulfide.

Reduction of the sulfur in the extracted AVS components to yield hydrogen sulfide can be achieved by reductive desulfurization via heating, such as heating on a laboratory heating mantle up to 109° C. The hydrogen sulfide may be condensed and trapped by standard zinc acetate solution. In some cases, the hydrogen sulfide is stored (for example, at 4° C.) for later quantification. The amount of sulfur in the hydrogen sulfide can be quantified as described in operation 110 of process 100.

Figure 3:
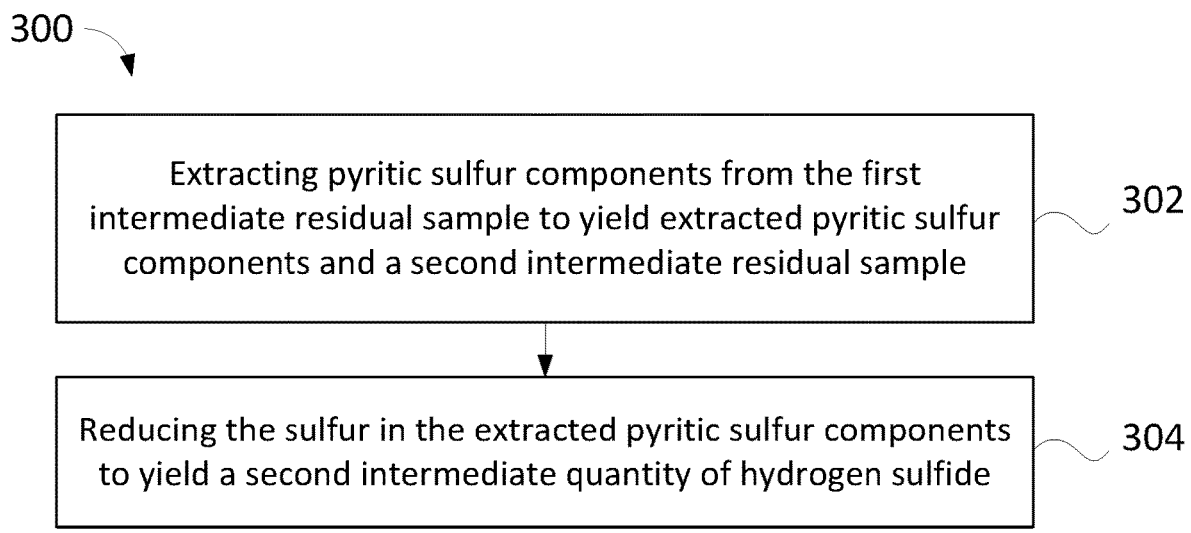
FIG. 3 is a flowchart showing operations in a process for treating the first intermediate residual sample described with respect to FIG. 2.

FIG. 3 is a flowchart showing operations in process 300 for treating the first intermediate residual sample described with respect to FIG. 2. In 302, pyritic sulfur components, such as iron disulfide ($FeS_2$), are extracted from the first intermediate residual sample to yield extracted pyritic sulfur components and a second intermediate dissolved and solid residual sample. Extracting pyritic sulfur components typically includes contacting the first intermediate residual sample with an amount of chromium reduction acid distillation mixed solvent at a temperature and for a duration sufficient to extract at least about 99 wt % of the pyritic sulfur components from the first intermediate residual sample. Contacting can include mixing the first intermediate residual sample with the chromium reduction acid distillation mixed solvent to yield a mixture and agitating the mixture. A suitable chromium reduction acid distillation mixed solvent includes an aqueous mixture of chromium chloride ($CrCl_3$), hydrochloric acid, and granular zinc metal. A suitable temperature of the chromium reduction acid distillation mixed solvent is in a range between 105° C. and 110° C. A suitable duration of contacting the first intermediate residual sample with the chromium reduction acid distillation mixed solvent is 1 to 3 h. In one example, a duration of contacting the sample with the chromium reduction acid distillation mixed solvent is about 2 h. For a chromium reduction acid mixed solvent including 10 mL of 1M chromium chloride, 5 g granular zinc metal, and 15 mL of 1M hydrochloric acid at a temperature in a range between 105° C. and 110° C., 10 to 15 mL of chromium reduction acid distillation mixed solvent is sufficient to extract pryritic sulfur components from 1 g of the first intermediate residual sample from operation 204 of process 200.

In 304, the sulfur in the extracted pyritic sulfur components is reduced to yield a second intermediate quantity of hydrogen sulfide that is captured as zinc sulfide. The zinc sulfide may be condensed and stored (for example, at 4° C.) for later quantification. The amount of sulfur in the hydrogen sulfide can be quantified as described in operation 110 of process 100.

Figure 4:
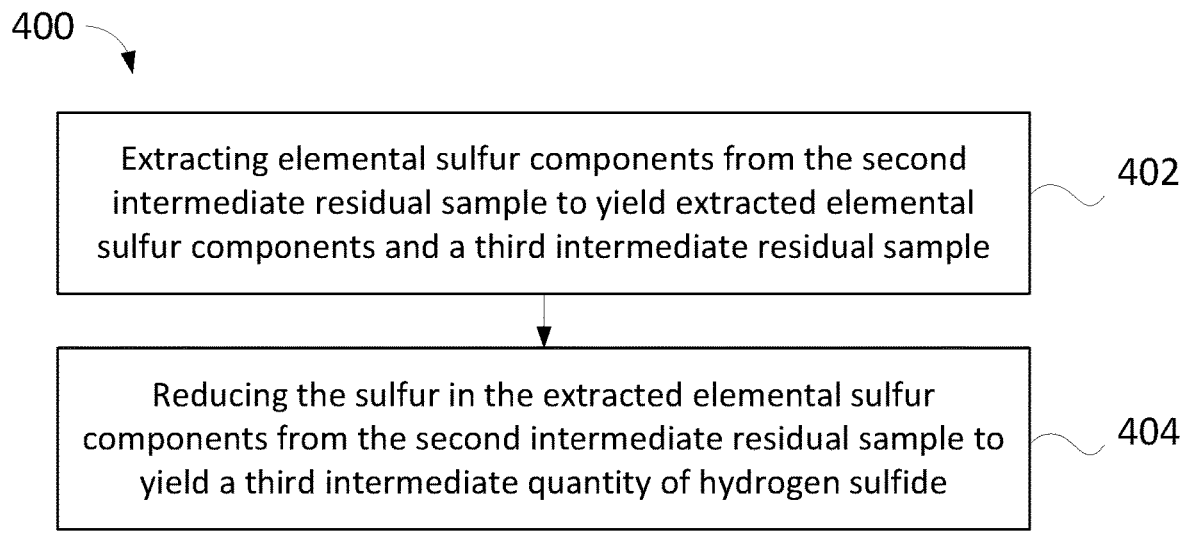
FIG. 4 is a flowchart showing operations in a process for treating the second intermediate residual sample described with respect to FIG. 3.

FIG. 4 is a flowchart showing operations in process 400 for treating the second intermediate residual sample described with respect to FIG. 3. In 402, elemental sulfur components, such as octasulfur ($S_8$) or zero-valent sulfur, are extracted from the second intermediate residual sample to yield extracted elemental sulfur components and a third intermediate residual sample. Extracting elemental sulfur components from the second intermediate residual sample typically includes contacting the second intermediate residual sample with an amount of a solution of chloroform and methanol at a temperature and for a duration sufficient to extract at least about 96 wt % of the elemental sulfur components from the second intermediate residual sample. Contacting can include mixing the second intermediate residual sample with the solution of chloroform and methanol to yield a mixture and agitating the mixture. The solution of chloroform and methanol extracts dissolved and colloidal elemental sulfur from the second intermediate residual sample. A suitable solution of chloroform and methanol is a solution including chloroform and methanol in a 1:1 volume ratio, however other ratios may also be used. A suitable temperature of the solution of chloroform and methanol is in a range between 95° C. and 105° C. In one example, a temperature of the solution of chloroform and methanol is in a range between 96° C. and 102° C. A suitable duration of contacting the second intermediate residual sample with the solution of chloroform and methanol is 1 to 3 h. In one example, a duration of contacting the second intermediate residual sample with the solution of chloroform and methanol is about 2 h. For a solution of chloroform and methanol in a 1:1 volume ratio at a temperature in a range between 96° C. and 102° C., 20 mL of the solution of chloroform and methanol is sufficient to extract 1 to 2 g of elemental sulfur components from the second intermediate residual sample. The resulting sulfur-containing solution of chloroform and methanol may be concentrated, for example, to 10 mL.

In 404, the sulfur in the elemental sulfur components in the sulfur-containing solution of chloroform and methanol is reduced to yield a third intermediate quantity of hydrogen sulfide products. The hydrogen sulfide is condensed and captured as zinc sulfide. In some cases, the zinc sulfide is stored (for example, at 4° C.) for later quantification. The amount of sulfur in the hydrogen sulfide can be quantified as described in operation 110 of process 100.

Figure 5:
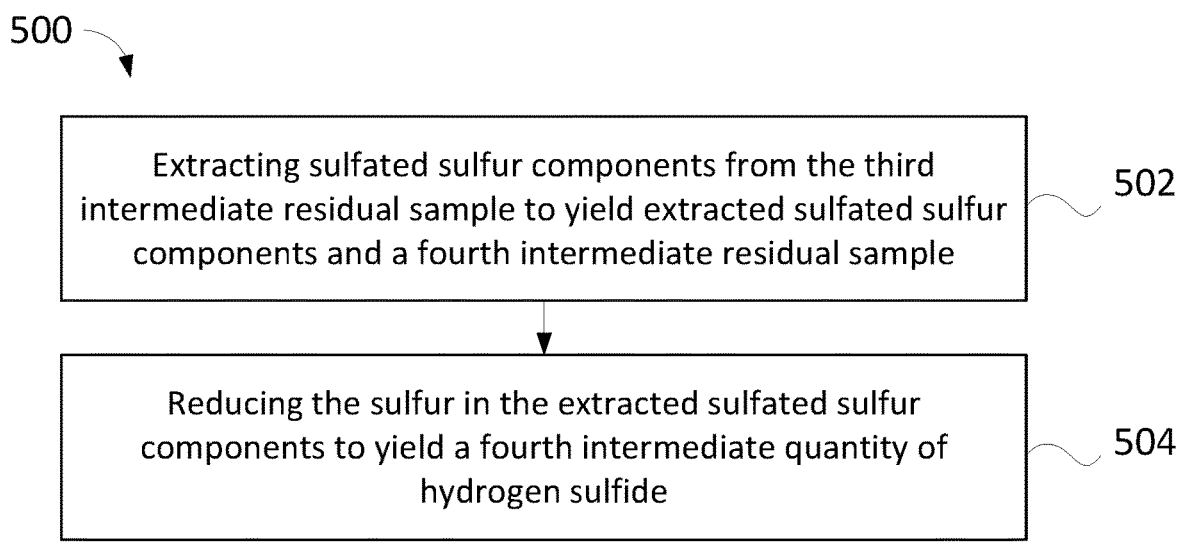
FIG. 5 is a flowchart showing operations in a process for treating the third intermediate residual sample described with respect to FIG. 4.

FIG. 5 is a flowchart showing operations in process 500 for treating the third intermediate residual sample described with respect to FIG. 4. In 502, sulfated sulfur components, such as components including $SO_4^{2-}$, are extracted from the third intermediate residual sample to yield extracted sulfated sulfur components and a fourth intermediate dissolved and solid residual sample. Extracting sulfated sulfur components from the third intermediate residual sample typically includes combining the sample with an aqueous solution of barium chloride at room temperature and for a duration sufficient to precipitate at least 99 wt % of the sulfated sulfur components from the third intermediate residual sample as barium sulfate. Contacting can include mixing the third intermediate residual sample with the aqueous solution of barium chloride to yield a mixture and agitating the mixture, then allowing barium sulfate in the mixture to precipitate. A suitable concentration of the aqueous solution of barium chloride is 1M, however other concentrations may also be used. The aqueous solution of barium chloride may be at room temperature. A suitable duration of contacting the third intermediate residual sample with the aqueous solution of barium chloride is 1 to 3 h. In one example, a duration of contacting the third intermediate residual sample with the aqueous solution of barium chloride is about 2 h. The resulting barium sulfate precipitate is collected, for example, by filtration. For 1M barium chloride at room temperature, 10 mL of barium chloride solution is sufficient to extract between about 1-2 g of sulfated components from the third intermediate residual sample.

In 504, the sulfur in the sulfated sulfur components is reduced to yield a fourth intermediate quantity of hydrogen sulfide. Reduction of the sulfur in the barium sulfate may be achieved by contacting the barium sulfate with an amount of a strong acid at a temperature and for a duration sufficient to reduce at least 99 wt % of the sulfur in the barium sulfate from the sample. Contacting can include mixing the barium sulfate with the strong acid to yield a mixture and agitating the mixture. A suitable strong acid includes a mixture of hydroiodic acid, hydrochloric acid, and phosphoric acid. In one example, the strong acid includes 7.5M hydroiodic acid (HI), 12.1M hydrochloric acid (HCl), and 14.8M phosphoric acid ($H_3PO_4$) in a volume ratio of 2:6:2, however other concentrations and ratios may also be used. A suitable temperature of the strong acid is in a range between 110° C. and 115° C. In one example, a temperature of the strong acid is 112° C. A suitable duration of contacting the third intermediate residual sample with the strong acid is 1 to 4 h. In one example, a duration of contacting the sample with the hydrochloric acid is 2.5 to 3 h. For a mixture of 7.5M hydroiodic acid, 12.1M hydrochloric acid, and 14.8M phosphoric acid in a volume ratio of 2:6:2 at a temperature of 112° C., 15-20 mL of the strong acid is sufficient to convert the sulfated sulfur into hydrogen sulfide. The hydrogen sulfide is condensed and captured as zinc sulfide. In some cases, the zinc sulfide is stored (for example, at 4° C.) for later quantification. The amount of sulfur in the hydrogen sulfide can be quantified as described in operation 110 of process 100.

In some implementations, operations 102 and 104 in process 100 include processes 200, 300, 400, and 500, such that the fourth intermediate residual sample of process 500 is the residual sample of process 100. That is, AVS, pyritic, elemental, and sulfated sulfur components are removed sequentially from the sample of process 100 and reduced, as described with respect to FIGS. 2-5, respectively, to yield the fourth intermediate residual sample. Extracting the organic sulfur components from the residual sample (that is, the fourth intermediate residual sample) may include sequentially extracting bitumen sulfur components and kerogen sulfur components from the residual sample, as described with respect to FIGS. 6 and 7.

Figure 6:
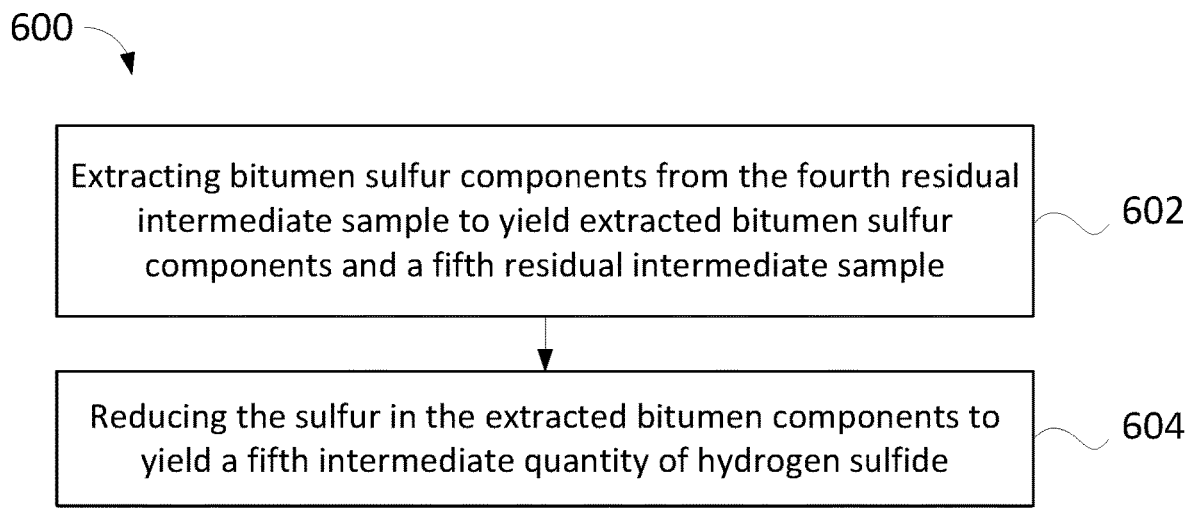
FIG. 6 is a flowchart showing operations in a process for treating the fourth intermediate residual sample described with respect to FIG. 5.

FIG. 6 is a flowchart showing operations in process 600 for treating the fourth intermediate residual sample described with respect to FIG. 5. In 602, bitumen sulfur components are extracted from the fourth intermediate residual sample to yield extracted bitumen sulfur components and a fifth intermediate residual sample. A solvent can be used to extract bitumen sulfur components from the fourth intermediate residual sample. Suitable solvents include solvents with high polarity and in which bitumen sulfur components in the fourth intermediate residual sample are soluble, such as an azeotropic mixture of dichloromethane and methanol, such as a mixture of dichloromethane and methanol in a 1:1 volume ratio. In one example, a mixture of 50 mL dichloromethane and 50 mL methanol can be used to remove approximately 2 g of a bitumen sulfur component fraction via continuous soxhlet extraction for a suitable length of time, such as 3 h. The dichloromethane-methanol extract layer may be separated, for example, via a separatory funnel. The extract layer may be concentrated, for example to 10 mL.

In 604, the sulfur in the extracted bitumen sulfur components is reduced to yield a fifth intermediate quantity of hydrogen sulfide. Reduction of the sulfur in the extracted bitumen sufur components to yield hydrogen sulfide can be achieved by reductive desulfurization. The solvent extract or concentrated solvent extract from 602 can be combined with activated Raney nickel catalyst to yield nickle sulfide. The nickel sulfide can be converted to hydrogen sulfide by addition of hydrochloric adic and heating. In one example, 10 mL of concentrated solvent extract from 602 was combined with 1 g of activated Raney nickel (Ni—H$_2$) catalyst, and 20 mL of concentrated hydrochloric acid was added dropwise to convert the nickel sulfide into hydrogen sulfide upon heating up to 98° C. for 1.5 h. The hydrogen sulfide may be condensed. In some cases, the hydrogen sulfide is stored for later quantification. The amount of sulfur in the hydrogen sulfide can be quantified as described in operation 110 of process 100.

Figure 7:
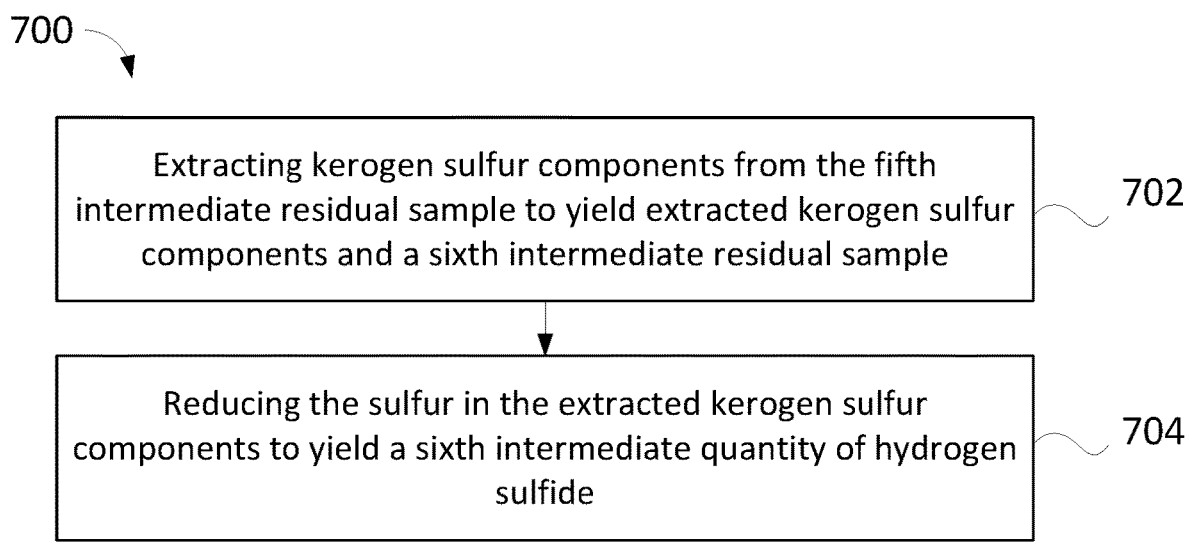
FIG. 7 is a flowchart showing operations in a process for treating the fifth intermediate residual sample described with respect to FIG. 6.

FIG. 7 is a flowchart showing operations in process 700 for treating the fifth intermediate residual sample described with respect to FIG. 6. In 702, kerogen sufur components are extracted from the fifth intermediate residual sample to yield extracted kerogen sulfur components and a sixth intermediate residual sample.

In 704, the sulfur in the extracted kerogen sulfur components is reduced to yield a sixth intermediate quantity of hydrogen sulfide. Reduction of the sulfur in the extracted kerogen sufur components to yield hydrogen sulfide can be achieved by reductive desulfurization. The extracted kerogen sulfur components from 702 can be combined with activated Raney nickel catalyst to yield nickle sulfide. The nickel sulfide can be converted to hydrogen sulfide by addition of hydrochloric adic and heating. In one example, 2.1 g of kerogen sulfur components from 702 was combined with 25 mL ethanol, 1 g Raney nickel, and 1.2 g bayerite (Al(OH)$_3$) as a reducing agent, and 20 mL of concentrated hydrochloric acid was added dropwise to convert nickel sulfide into hydrogen sulfide upon heating up to 98° C. for 1.5 h. The hydrogen sulfide is condensed and captured as zinc sulfide. In some cases, the zinc sulfide is stored (for example, at 4° C.) for later quantification. The amount of sulfur in the hydrogen sulfide can be quantified as described in operation 110 of process 100.

EXAMPLES

Figure 8:
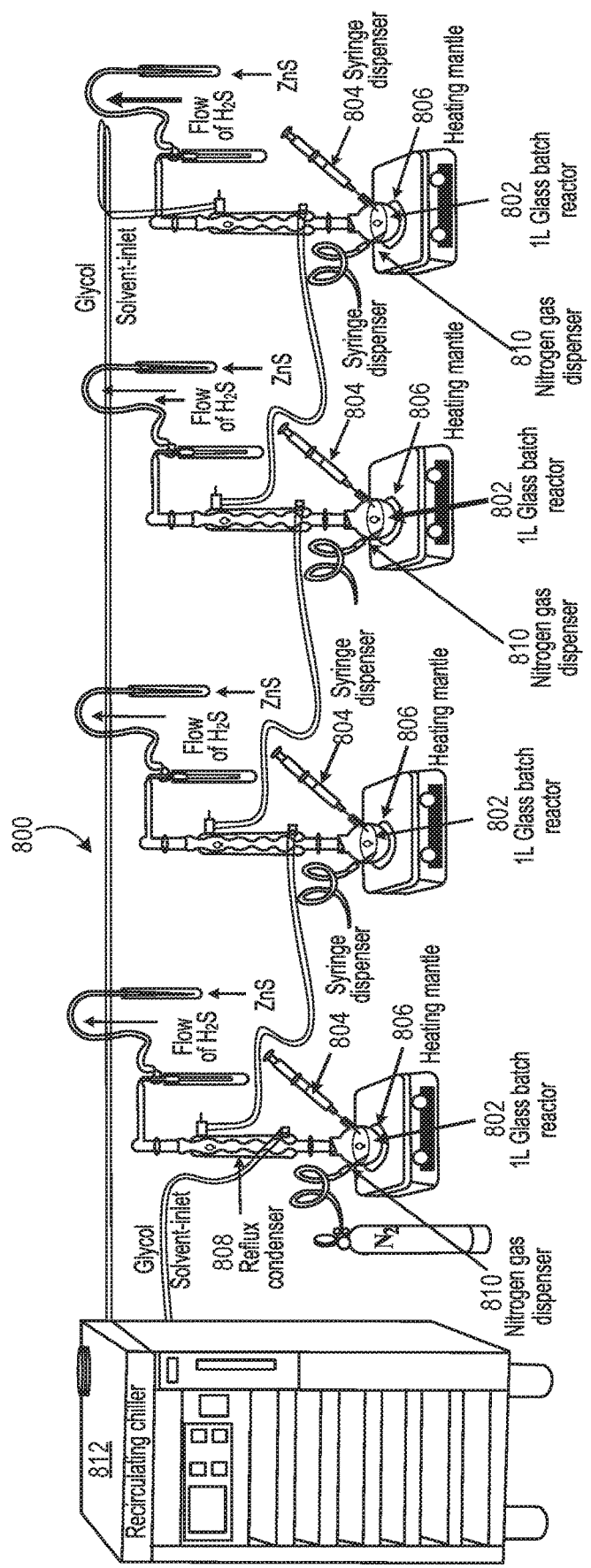
FIG. 8 depicts sequential extraction apparatus for sulfur species extraction and quantification in petroleum materials.

Process 100 was used to quantify sulfur in petroleum source rock samples from a selected formation. FIG. 8 depicts sequential extraction apparatus 800 for the implementation of process 100, including chemical reaction of the petroleum source rock samples with mixed chemical reagents, reductive desulfurization via heating to convert the inorganic and organic sulfur components into hydrogen sulfide, condensation of the hydrogen sulfide, transfer of reduced hydrogen sulfide into capturing solutions via nitrogen purging, and quantitative analysis of the sulfur content in each capturing solution. Sequential extraction apparatus 800 includes 1 L three-neck glass batch reactors 802, syringe dispensers 804 to aliquot chemical reagents into batch reactors 802, heating systems 806, reflux condensing system 808, and nitrogen gas dispenser 810. Reflux condensing system 808 is an Allihn-style condenser connected to recirculating chiller 812. Sequential extractions in this example include six successive sequential extractions with different chemical extractants listed in Table 1 shown in FIG. 9. Table 1 also lists the volume of hydrogen sulfide capturing solutions and the time to reductively desulfurize each sulfur component.

A set of 20 well preserved drill core samples from Locations 1 (Samples L11-L110), 2 (Samples L21-L25), and 3 (Samples L31-L35) in the formation. Samples of about 5 to 10 g, prepared by cutting and crushing, were ground into powder for different sulfur speciation analyses. The major inorganic sulfur fractions in the source rocks, AVS (consisting mainly of pyrrhotite (Fe$_{(1-x)}$S)) and pyritic sulphur (FeS$_2$) were sequentially extracted with 25 mL of 5 Normal (N) HCl and chromium reduction acid distillation, respectively.

After removal of all AVS and pyritic iron sulfur species, dissolved elemental sulfur (S$_8$) was extracted from the supernatant solution and residual sediments by treating the sample twice with 100 mL successive portions of a solvent mixture having a 1:1 volume ratio of chloroform and methanol. This solvent mixture is suitable for extracting dissolved and colloidal elemental sulfur in the solid phase. The chloroform/methanol extract containing the elemental sulfur was separated in separatory funnel, concentrated to 10 mL on a rotatory evaporator, and reduced via distillation to $H_2S$ using 1:1 mixture of ethanol and acidic chromium chloride solution.

Dissolved sulfated sulfur present in the aqueous and sedimentary samples were converted into a barium sulfate ($BaSO_4$) precipitate by addition of 10 mL of a solution of 1M barium chloride. Sulfur present in the $BaSO_4$ was quantified accurately by reductive distillation into $H_2S$, using 30 mL of a $HI/HCl/H_3PO_4$ mixture (volume ratio 2:6:2).

Organic-bound sulfur fractions (mainly bitumen sulfur and kerogen sulfur) in the residual sediment were separated and quantified. An azeotropic mixture of dichloromethane and methanol was used to separate bitumen sulfur from the sediment by continuous soxhlet extraction for 48 h. The resulting solvent extracts were concentrated to 10 mL on a rotor-evaporator, and then the bitumen sulfur components were reduced by Raney nickel hydro-desulfurization to hydrogen sulfide ($H_2S$). The kerogen sulfur components in the residual material was isolated using a mixture of Raney nickel and bayerite as a reducing agent.

Reductive distillation tests for each sulfur species were carried out for between 2-3 h in a reaction flask. Each mixture was heated under reflux to slowly release $H_2S$, which was captured as zinc sulfide (ZnS). Quantitative analysis of the sulfur in the zinc sulfide was achieved by UV-VIS spectrophotometric methods. Table 2 in FIG. 10 lists the amount of sulfur present in each sample as AVS, pyritic, elemental, sulfated, bitumen, and kerogen sulfur components. A total amount of sulfur in each sample is provided as the sum of all contributions for each sample.

The total sulfur amounts in Table 2 were compared with previously existing standard methods by using Vario Elemental Analyzer (EA) combustion techniques for analyses of total sulfur content. The results obtained for the same samples, together with the detection limit (expressed in weight percent of sulfur per dry petroleum sediments) are listed in Table 3 in FIG. 11. A minimum detection limit of 0.16 ppm by weight was separately tested for methylene blue sulfur speciation analysis for low sulfur bearing petroleum materials. From Table 3, it is apparent that the total sulfur amounts determined by sequential extraction typically exceeded the total sulfur amounts determined by elemental analysis with mean error variation ranging from 0.1 wt % to 0.2 wt %. This suggests that the sulfur content, as determined by Vario Elemental Analyzer (EA) combustion methods, is easily influenced by the variability of the sample matrix, with organic and inorganic materials in the sample leading to incomplete combustion, leakages in the pyrolysis tube, or both.

Results for various ratios of the chemical reagent to sulfur content revealed that, for a starting sample size of 5 to 10 g of petroleum source rock, superior results were achieved with 30 mL extractant reagent volumes. An optimal temperature for the chemical reactions was about 112° C. Sulfur quantification was less accurate for reactions conducted at temperatures less than 100° C.

Thus, particular implementations of the subject matter have been described. Other implementations are within the scope of the claims.

What is claimed is:

1. A method for quantifying an amount of sulfur in a sample comprising inorganic sulfur components and organic sulfur components, the method comprising:

extracting inorganic sulfur components from the sample to yield extracted inorganic sulfur components and a residual sample, wherein the sample is of sulfur-bearing petroleum material comprising a petroleum source rock or a hydrocarbon condensate;

reducing the sulfur in the extracted inorganic sulfur components to yield a first quantity of hydrogen sulfide;

extracting organic sulfur components comprising a kerogen-bound sulfur component and a bitumen-bound sulfur component from the residual sample to yield extracted organic sulfur components;

reducing the sulfur in the extracted organic sulfur components to yield a second quantity of hydrogen sulfide; and quantifying the amount of sulfur in the first quantity of hydrogen sulfide and the second quantity of hydrogen sulfide.

2. The method of claim 1, wherein extracting the inorganic sulfur components from the sample comprises sequentially extracting acid volatile sulfur components, pyritic sulfur components, sulfated sulfur components, and elemental sulfur components from the sample.

3. The method of claim 1, wherein:

extracting the inorganic sulfur components from the sample to yield the extracted inorganic sulfur components and the residual sample comprises extracting acid volatile sulfur components from the sample to yield extracted acid volatile sulfur components and a first intermediate residual sample, and reducing the sulfur in the extracted inorganic sulfur components to yield the first quantity of hydrogen sulfide comprises reducing the sulfur in the extracted volatile sulfur components to yield a first intermediate quantity of hydrogen sulfide.

4. The method of claim 3, wherein the acid volatile sulfur components comprise at least one of hydrogen sulfide ($H_2S$), bisulfide ($HS^-$), disulfide ($S^{2-}$), and iron sulfide (FeS).

5. The method of claim 3, wherein extracting the acid volatile sulfur components from the sample comprises contacting the sample with hydrochloric acid.

6. The method of claim 3, wherein:

extracting the inorganic sulfur components from the sample to yield the extracted inorganic sulfur components and the residual sample further comprises extracting pyritic sulfur components from the first intermediate residual sample to yield extracted pyritic sulfur components and a second intermediate residual sample, and reducing the sulfur in the extracted inorganic sulfur components to yield the first quantity of hydrogen sulfide further comprises reducing the sulfur in the extracted pyritic sulfur components to yield a second intermediate quantity of hydrogen sulfide.

7. The method of claim 6, wherein the pyritic sulfur components comprise iron disulfide ($FeS_2$).

8. The method of claim 6, wherein extracting the pyritic sulfur components from the first intermediate residual sample comprises contacting the first intermediate residual sample with chromium reduction acid distillation mixed solvents.

9. The method of claim 6, wherein:

extracting the inorganic sulfur components from the sample to yield the extracted inorganic sulfur components and the residual sample further comprises extracting elemental sulfur components from the second intermediate residual sample to yield extracted elemental sulfur components and a third intermediate residual sample, and reducing the sulfur in the extracted inorganic sulfur components to yield the first quantity of hydrogen sulfide further comprises reducing the sulfur in the extracted elemental sulfur components to yield a third intermediate quantity of hydrogen sulfide.

10. The method of claim 9, wherein the elemental sulfur components comprise octasulfur (S8), zero-valent sulfur, or both.

11. The method of claim 9, wherein extracting the elemental sulfur components from the second intermediate residual sample comprises contacting the second intermediate residual sample with a mixture of chloroform and methanol.

12. The method of claim 9, wherein:
extracting the inorganic sulfur components from the sample to yield the extracted inorganic sulfur components and the residual sample further comprises extracting sulfated sulfur components from the third intermediate residual sample to yield extracted sulfated sulfur components and a fourth intermediate residual sample, and reducing the sulfur in the extracted inorganic sulfur components to yield a first quantity of hydrogen sulfide further comprises reducing the sulfur in the extracted sulfated sulfur components to yield a fourth intermediate quantity of hydrogen sulfide.

13. The method of claim 12, wherein the sulfated sulfur components comprise $SO_4^{2-}$.

14. The method of claim 12, wherein:
extracting the sulfated sulfur components comprises forming a sulfate precipitate, and reducing the sulfur in the extracted sulfated sulfur components to yield the fourth intermediate quantity of hydrogen sulfide comprises reducing the sulfate in the sulfate precipitate to yield elemental sulfur, and reducing the elemental sulfur from the sulfate precipitate.

15. The method of claim 1, wherein extracting the organic sulfur components from the residual sample comprises sequentially extracting bitumen sulfur components and kerogen sulfur components from the residual sample.

16. The method of claim 1, wherein:
extracting the organic sulfur components from the residual sample to yield the extracted organic sulfur components comprises extracting, via a solvent, bitumen sulfur components from the residual sample to yield extracted bitumen sulfur components and a fifth intermediate residual sample, and reducing the sulfur in the extracted organic sulfur components to yield the second quantity of hydrogen sulfide comprises reducing the sulfur in the extracted bitumen sulfur components to yield a fifth intermediate quantity of hydrogen sulfide.

17. The method of claim 16, wherein extracting the bitumen sulfur components from the residual sample comprises extracting the bitumen sulfur components from the residual sample with the solvent comprising an azeotropic mixture of dichloromethane and methanol to yield extracted bitumen sulfur components, and reducing the sulfur in the extracted bitumen sulfur components comprises reducing the sulfur in the extracted bitumen sulfur components via a Raney nickel desulfurization process.

18. The method of claim 16, wherein:
extracting the organic sulfur components from the residual sample to yield the extracted organic sulfur components comprises extracting kerogen sulfur components from the fifth intermediate residual sample to yield extracted kerogen sulfur components; and reducing the sulfur in the extracted organic sulfur components to yield the second quantity of hydrogen sulfide further comprises reducing the sulfur in the extracted kerogen sulfur components to yield a sixth intermediate quantity of hydrogen sulfide.

19. The method of claim 18, wherein reducing the sulfur in the extracted kerogen sulfur components comprises using a modified Raney nickel and bayerite as a reducing agent.

20. The method of claim 1, wherein quantifying the amount of sulfur in the first quantity of hydrogen sulfide comprises contacting the first quantity of hydrogen sulfide with a zinc acetate buffer solution to yield zinc sulfide, and quantifying the amount of sulfide in the zinc sulfide.

21. The method of claim 20, wherein quantifying the amount of sulfide in the zinc sulfide comprises a colorimetric determination.

22. The method of claim 1, wherein the sample comprises a solid, a liquid, or a mixture thereof.

* * * * *